United States Patent
Loock et al.

(10) Patent No.: US 7,391,942 B2
(45) Date of Patent: Jun. 24, 2008

(54) LONG PERIOD GRATING SENSOR METHODS AND APPARATUS

(75) Inventors: Hans-Peter Loock, Kingston (CA); R. Stephen Brown, Kingston (CA); John A. Barnes, Kingston (CA); Nicholas R. Trefiak, Kingston (CA); Krista L. Laugesen, Kingston (CA); Galina Nemova, Montreal (CA)

(73) Assignee: Queen's University at Kingston, Kingston (CA)

( * ) Notice: Subject to any disclaimer, the term of this patent is extended or adjusted under 35 U.S.C. 154(b) by 152 days.

(21) Appl. No.: 11/145,182

(22) Filed: Jun. 6, 2005

(65) Prior Publication Data

US 2005/0269490 A1 Dec. 8, 2005

(51) Int. Cl.
*G02B 6/00* (2006.01)
*G02B 6/34* (2006.01)

(52) U.S. Cl. .............................................. 385/37; 385/2

(58) Field of Classification Search ................... 385/37, 385/2
See application file for complete search history.

(56) References Cited

U.S. PATENT DOCUMENTS

| 5,864,641 | A * | 1/1999 | Murphy et al. ................. 385/12 |
| 6,021,240 | A | 2/2000 | Murphy et al. |
| 6,058,226 | A | 5/2000 | Starodubov |
| 6,343,168 | B1 | 1/2002 | Murphy et al. |
| 2003/0103727 | A1 * | 6/2003 | Ishikawa et al. ............... 385/37 |
| 2004/0086216 | A1 | 5/2004 | Elster et al. |

OTHER PUBLICATIONS

Brown, R.S., et al., "Fiber-loop ring-down spectroscopy." *Journal of Chemical Physics* 117: 10444-10447 (2002).
Mayer, P., et al., "Absorption of hydrophobic compounds into the poly(dimethylsiloxane) coating of solid-phase microextraction fibers: high partition coefficients and fluorescence microscopy images." *Anal. Chem.* 72: 459-464 (2000).
Pilla, P., et al., "Optical chemo-sensor based on long period gratings coated with δ form syndiotatic polystyrene." *IEEE Photonics Technology Letters* 17: 1713-1715 (2005).
Tong, Z., et al., "Fiber-loop ring-down spectroscopy: a sensitive absorption technique for small liquid samples." *Review of Scientific Instruments* 74: 4818-4826 (2003).

(Continued)

*Primary Examiner*—M. R. Connelly-Cushwa
*Assistant Examiner*—Rhonda S Peace
(74) *Attorney, Agent, or Firm*—Stephen J. Scribner; Carl Miernicki Steeg

(57) ABSTRACT

The invention relates to optical sensors and systems and methods employing the sensors for detecting one or more compounds of interest in a test medium. In one embodiment an optical sensor comprising a long period grating and a solid phase microextraction (SPME) film is exposed to a test medium such that one or more compounds of interest are selectively partitioned into the solid phase microextraction film. At least one optical property of the sensor exposed to the test medium is compared with at least one corresponding optical property of the sensor in absence of the test medium; wherein a difference in the optical property is indicative of one or more compounds of interest in the test medium. The methods and systems may employ long period grating sensors with or without SPME films, and fiber loop ring-down spectroscopy to measure optical properties of the sensor.

13 Claims, 9 Drawing Sheets

OTHER PUBLICATIONS

Achaerandio, M., et al., "Electrostatic self-assembled thin films deposited on optical fiber long-period gratings for the fabrication of chemical sensors." *Proceedings of SPIE 5502*: 300-303 (2004).

Allsop, T., et al., "Detection of organic aromatic compounds in paraffin by a long-period fiber grating optical sensor with optimized sensitivity." *Optics Communications* 191: 181-190 (2001).

Atkinson, D.B., "Solving chemical problems of environmental Importance using cavity ring-down spectroscopy." *Analyst* 128: 117-125 (2003).

Berden, G., et al., "Cavity ring-down spectroscopy: experimental schemes and applications." *Int. Reviews in Physical Chemistry* 19: 565-607 (2000).

Chen, X., et al., "Optical biochemical sensors based on long-period fibre gratings UV-inscribed in D-fiber with enhanced sensitivity by HF etching process." *Proceedings of SPIE* 5486: 187-191 (2004).

Chong, J.H., et al., "Measurements of refractive index sensitlity using long-period grating refractometer." *Optics Communications* 229: 65-69 (2004).

Cooper, K.R., "Long-term evaluation of a fiber optic-based irreversible moisture sensor." *Proceedings of SPIE* 5384 64-70 (2004).

Elster, J., et al., "Optical fiber-based adhesive bondline monitoring system for composite patch systems." *Proceedings of SPIE* 4335: 188-195 (2001).

Goswami, K., et al., "Optical sensor for detecting missile fuel leaks." *Proceedings of SPIE* 4040: 83-94 (2000).

Greene, J., et al., "Optical fiber corrosion sensors for aging aircraft." *Proceedings of SPIE* 3399: 28-33 (1998).

Gupta, M., et al., "Cavity-enhanced spectroscopy in optical fibers." *Optics Letters* 27: 1878-1880 (2002).

Hou, R., et al., "Modelling of long-period fibre grating response to refractive index higher than that of cladding." *Meas. Sci. Technol.* 12: 1709-1713 (2001).

James, S.W., et al., "Optical fibre long-period grating sensors: characteristics and application." *Meas. Sci. Technol.* 14: R49-R61 (2003).

James, S.W., et al., "Cryogenic temperature response of fibre optic long period gratings." *Meas. Sci. Technol.* 14: 1408-1411 (2003).

Luo, S., et al., "Applications of LPG fiber optical sensors for relative humidity and chemical warfare agents monitoring." *Proceedings of SPIE* 4920: 193-204 (2002).

Namboodiri, V.V., et al., "Refractive index measurement using multimode fibers with long period grating." *Proceedings of SPIE* 5459: 415-419 (2004).

Zhou, K., et al., "High-sensitivity optical chemosensor based on etched D-fibre Bragg gratings." *Electronic Letters* 40: 232-233 (2004).

* cited by examiner

LONG PERIOD GRATING SENSOR METHODS AND APPARATUS

FIELD OF THE INVENTION

This invention relates to optical sensors based on long period gratings. In particular, the invention provides methods, sensors, and systems for optical sensors based on long period gratings interrogated by optical waveguide loop ring-down spectroscopy, and/or coated with a solid phase microextraction film.

BACKGROUND OF THE INVENTION

Long period gratings (LPGs), like fiber Bragg gratings (FBGs), are periodic modulations of the refractive index of the core of an optical waveguide—typically a single-mode optical fiber—but the LPG has a much longer period (typically 10 μm to 1 mm) compared to the Bragg grating (<1 μm). LPGs couple light from the mode propagating along the fiber core to modes associated with co-propagating cladding modes of the fiber. Due to the high losses typically experienced by cladding modes, the LPG behaves as a notch filter. Thus, unlike FBGs which reflect wavelengths selected by the periodicity of the grating back along the core of the optical fiber, LPGs act as notch filters with low back reflection. Depending on the regularity of the grating period and the length of the grating, the band rejection of an LPG can have a width of typically 30 nm and the loss at the peak can approach −30 dB (James et al. 2003).

For a LPG, the wavelengths of the core mode that couples into the cladding modes are characterized by the phase-matching condition $$\lambda_f = \Lambda [n_{eff,core}(\lambda, n_1, n_2) - n_{eff,cladding}^i(\lambda, n_2, n_3)] \quad \text{(equation 1)}$$

where $n_{eff,core}$ is the effective core refractive index which is a function of wavelength, core refractive index $n_1$ and cladding refractive index $n_2$, and $n_{eff,cladding}$ is the effective cladding refractive index of the $i^{th}$ mode, which is a function of wavelength, cladding refractive index $n_2$ and surrounding refractive index $n_3$, and $\Lambda$ is the period of the LPG. From this expression it is apparent that any physical, mechanical, or environmental parameter that is capable of changing the effective refractive indices differentially (e.g., refractive index of the surrounding medium) or of changing the period of the grating (e.g., mechanical strain), will lead to a change in the attenuation spectrum of the LPG. Given proper calibration, one can then use the shift in the attenuation lines to interrogate the environmental parameter (see James et al., 2003). This measurement principle has been discussed in a number of publications, and has led to considerable interest in using LPGs as inexpensive, robust and sensitive sensors (Allsop et al. 2001; Bhatia et al. 1996; Bhatia 1999; Chong et al. 2004; DeLisa et al. 2000, Grubsky et al. 2000; James et al. 2003; Khaliq et al. 2001; Khaliq et al. 2002; Lee et al. 2003; Shu et al. 1999).

When using LPGs as chemical sensors the differential change in refractive index is typically induced by a changing refractive index of the medium surrounding the cladding. Since the evanescent wave of the cladding modes effectively "probes" the medium outside the fiber, its refractive index will also influence the effective refractive index of the cladding. If, for example, in an extreme case the refractive indices of cladding and surrounding medium are identical, the cladding loses its ability to guide light and will essentially be extended infinitely. LPGs can hence be used as sensitive sensors for changes in refractive indices (Bhatia 1999; Chong et al. 2004; Lee et al. 2003; Shu et al. 1999). For example, aromatic compounds in a hydrocarbon matrix have been detected by changes in an LPG spectrum (Allsop et al. 2001), producing a wavelength change of ~0.4 nm for a concentration of xylene of 0.5% (vol) in a paraffin solution. The detection limit was reported as 0.04% (~400 ppm).

One approach to the use of LPGs as sensors has been to coat the LPG with a reactive coating that undergoes a chemical and/or physical change when exposed to the analyte. For example, Luo et al. (2002) used LPGs coated with carboxymethylcellulose (CMC) to detect humidity, and LPGs coated with metal nanoclusters embedded in polyethylenimine (PEI) to detect sulfide-based chemical warfare agents. However, the CMC LPG sensors exhibited strong temperature dependence, and the PEI LPG sensors underwent an irreversible reaction with the sulfide, such that they were not re-usable. It is also likely that the PEI LPG sensors would cross-react with other sulfides/thiols, suggesting poor specificity to the target compound. Similarly, Murphy et al. (U.S. Pat. No. 5,864,641, issued Jan. 26, 1999) proposed a physically, electrically, and chemically reactive coatings for LPG sensors. Murphy et al. discussed such a coating populated with reactive sites for the binding and hence detection of protein, but did not demonstrate any specificity to a particular protein.

Clearly there are a number of obstacles, relating to factors such as temperature sensitivity, specificity to the target species, reversibility of interaction with the target species, and sensitivity with respect to refractive index, which must be overcome before LPGs may be used practically as sensors.

SUMMARY OF THE INVENTION

According to one aspect of the invention there is provided a method for detecting one or more compounds in a test medium, comprising: providing an optical sensor comprising a long period grating and a solid phase microextraction film; exposing the optical sensor to the test medium such that said one or more compounds of interest are selectively partitioned into the solid phase microextraction film; and comparing at least one optical property of the sensor exposed to the test medium with at least one corresponding optical property of the sensor in absence of the test medium; wherein a difference in said at least one optical property is indicative of detection of said one or more compounds.

In one embodiment, the long period grating is disposed on an optical fiber. In various embodiments, the optical fiber is a single-mode optical fiber, and the solid phase microextraction film comprises PDMS. In a preferred embodiment, partitioning of the one or more compounds of interest into the solid phase microextraction film is reversible.

In a further embodiment, the method further comprises providing an array of two or more optical sensors each comprising a long period grating and a solid phase microextraction film.

According to another aspect of the invention there is provided an optical sensor for detecting one or more compounds in a test medium, comprising: an optical waveguide comprising a long period grating; and a solid phase microextraction film disposed on said long period grating; wherein said one or more compounds are selectively partitioned into the solid phase microextraction film; and wherein said partitioning of said one or more compounds alters at least one optical property of the long period grating.

In one embodiment, the optical waveguide is an optical fiber. In various embodiments, the optical fiber is a single-mode optical fiber, and the solid phase microextraction film comprises PDMS. In a preferred embodiment, partitioning of the one or more compounds of interest into the solid phase microextraction film is reversible. In another embodiment, the sensor further comprises an array of two or more optical sensors each comprising a long period grating and a solid phase microextraction film.

According to another aspect of the invention there is provided a system for detecting one or more compounds in a test medium, comprising: one or more optical sensors as described above; a light source; a detector for detecting light having passed through said one or more sensors; and means for evaluating one or more properties of said detected light.

According to another aspect of the invention there is provided a method for detecting one or more compounds in a test medium, comprising: providing an optical sensor comprising a long period grating; measuring and comparing at least one optical property of the sensor exposed to the test medium with at least one corresponding optical property of the sensor in absence of the test medium, a result of said comparison being indicative of detection of the one or more compounds; wherein measuring at least one optical property comprises using fiber loop ring-down spectroscopy.

In one embodiment, the method further comprised disposing a solid phase microextraction film on the long period grating.

According to another aspect of the invention there is provided a method for detecting one or more compounds in a test medium, comprising: providing an optical sensor comprising a long period grating and a solid phase microextraction film; exposing the optical sensor to the test medium such that said one or more compounds are selectively partitioned into the solid phase microextraction film; and measuring and comparing at least one optical property of the sensor exposed to the test medium with at least one corresponding optical property of the sensor in absence of the test medium, a result of said comparison being indicative of detection of the one or more compounds; wherein measuring at least one optical property comprises using fiber loop ring-down spectroscopy.

In one embodiment, said fiber loop ring-down spectroscopy comprises: providing an optical waveguide loop attached to said optical sensor; launching in the optical waveguide loop an intensity-modulated light at a reference phase; detecting a phase of said light along the optical waveguide loop; and comparing the detected phase of said light along the loop with the reference phase; wherein comparing the detected phase and the reference phase provides information about said at least one optical property of the optical sensor.

In another embodiment, said fiber loop ring-down spectroscopy comprises: providing an optical waveguide loop attached to said optical sensor; illuminating the optical waveguide loop with a plurality of light pulses; detecting roundtrips of said light pulses at one or more locations along the loop; and determining ring-down time of said light pulses; wherein said ring-down time is indicative of at least one optical property of the optical sensor.

According to another aspect of the invention there is provided a system for detecting one or more compounds in a test medium, comprising: an optical sensor comprising a long period grating, the optical sensor having optical properties which are altered when exposed to the one or more compounds; an optical waveguide loop attached to said optical sensor; a light source for launching in the optical waveguide loop an intensity-modulated light at a reference phase; a detector for detecting a phase of said light along the optical waveguide loop; and means for comparing the detected phase of said light along the loop with the reference phase; wherein comparing the detected phase and the reference phase provides information about said optical properties of the optical sensor.

According to another aspect of the invention there is provided a system for detecting one or more compounds in a test medium, comprising: an optical sensor comprising a long period grating, the optical sensor having optical properties which are altered when exposed to the one or more compounds; an optical waveguide loop attached to said optical sensor; a light source for illuminating the optical waveguide loop with a plurality of light pulses; a detector for detecting roundtrips of said light pulses at one or more locations along the loop; and means for determining ring-down time of said light pulses; wherein said ring-down time is indicative of at least one optical property of the optical sensor.

In various embodiments, the above systems may further comprise a solid phase microextraction film disposed on said long period grating; wherein said one or more compounds are selectively partitioned into the solid phase microextraction film; and wherein said partitioning of the one or more compounds alters at least one optical property of the long period grating. In preferred embodiments of the above, partitioning of the one or more compounds of interest into the solid phase microextraction film is reversible.

In various embodiments of the above systems, the at least one optical property is refractive index, the light may be of at least one wavelength selected from infra-red (IR), visible, and ultra-violet, and the optical waveguide loop may comprise a single-mode optical fiber.

The methods and systems of the invention may employ a plurality of optical sensors as described above, the plurality of sensors being multiplexed and/or in an array, for detecting a plurality of compounds of interest. In further embodiments, individual sensors or groups of sensors may each have a solid phase microextraction film corresponding to a distinct compound of interest.

BRIEF DESCRIPTION OF THE DRAWINGS

The invention will be described below, by way of example, with reference to the accompanying drawings, wherein.

DETAILED DESCRIPTION OF PREFERRED EMBODIMENTS

Figure 1:
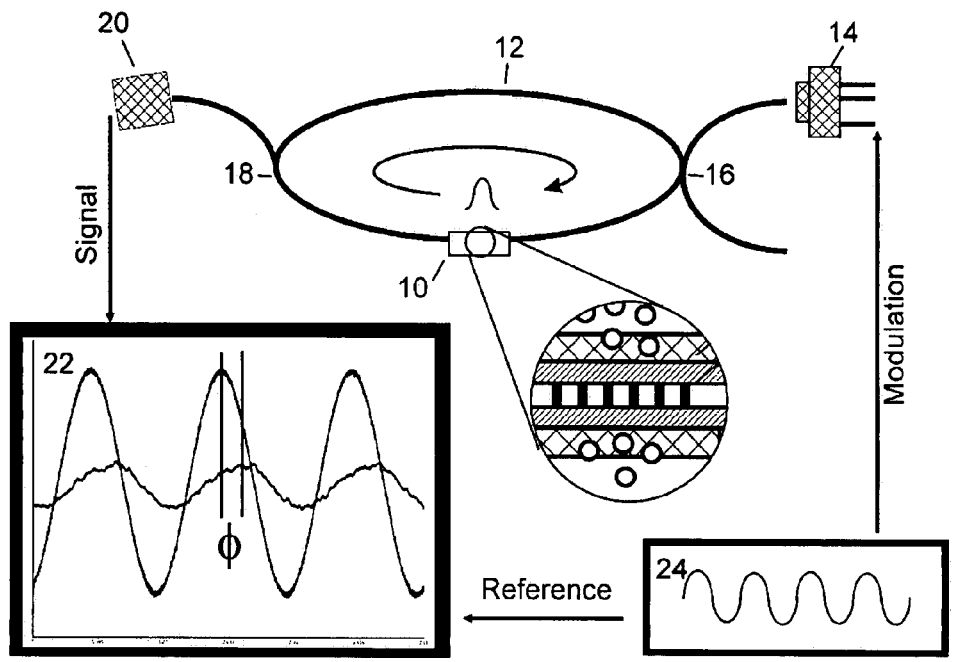
FIG. 1 is a schematic diagram of an experimental setup incorporating a LPG into a fiber optic ring-down spectroscopy loop.

Practical use of LPGs as sensors in, for example, environmental and chemical applications, requires monitoring the change in the attenuation spectrum of the LPG as a function of the composition of the medium surrounding the LPG. Here, five obstacles need to be addressed:

(i) The change in the attenuation spectrum is largest when the refractive index of the cladding and the surrounding medium is similar. This excludes water and other solvents as a matrix in which contaminants can be measured, as their refractive indices are considerably below the refractive index of the cladding.

(ii) If the index matching condition is not fulfilled, the changes in the attenuation spectrum may be very small and measurable only with a highly resolving spectrum analyzer.

(iii) There is no chemical specificity that allows the operator to identify which chemical compound has induced a shift in the attenuation spectrum.

(iv) The equipment needed to determine the change in the attenuation spectrum is expensive and not necessarily field suitable.

(v) Measurable refractive index changes typically require high concentration changes (hundreds of ppm) in the surrounding media. A LPG is therefore not suitable as a detector for applications involving trace amounts of contaminants.

The invention addresses these concerns in providing an inexpensive, robust, and sensitive sensor employing an LPG together with at least one of solid phase microextraction and fiber-loop ring-down spectroscopy.

As used herein, the term "solid phase microextraction (SPME)" relates to the extraction or partitioning of a compound of interest (e.g., an analyte or target species) from a mixture of compounds, into a solid phase, based on affinity of the compound of interest for the solid phase. Preferably, partitioning of the compound of interest into the solid phase material is reversible. The term "affinity" as used herein does not refer to interaction characteristic of protein-ligand complexes, as SPME does not involve such reactions. The solid phase material does not react with the compound of interest, and accordingly does not undergo a chemical change when exposed to the compound of interest. Rather, SPME is based on partitioning of the compound of interest from a mixture or medium into the solid phase. Such partitioning may involve the compound dissolving into the solid phase, wherein compound particles become substantially surrounded by the solid phase. Without being bound by theory, it is believed that at least in some situations such partitioning is based on the free energy gain of the system when the molecule of interest leaves the mixture or medium and moves into the solid phase. For example, in an aqueous system, unfavourable interactions of a compound of interest with water may drive the transfer (i.e., entropy). The mixture of compounds is typically a fluid, and may be a gas or a liquid. Where the fluid is a liquid, the mixture may be aqueous. The compound of interest may itself be a solid, liquid, or gas, e.g., dispersed as particles in the mixture of compounds.

In optical sensor applications, the solid phase material is applied, e.g., as a film, to the outside surface of an optical waveguide, such as an optical fiber. Compounds of interest partitioned into the solid phase material detectably alter at least one optical property of the fiber, thus rendering the fiber an optical sensor for the compound of interest. The affinity of the compound of interest for the solid phase material is characterized as the film:solution partition constant ($K_{fs}$), defined as the ratio of the concentration of a compound in the film to the concentration of the compound in solution at equilibrium. Selectivity of a film for one compound over another is then defined as the ratio of $K_{fs}$ values ($=K_{fs,a}/K_{fs,b}$).

An example of a SPME film material is the polymer polydimethylsiloxane (PDMS), which extracts compounds from a mixture of compounds in close correlation to hydrophobicity. This is best described by the close correlation between $K_{fs}$ for compounds in PDMS films and $K_{ow}$, the octanol:water partition constant (Mayer et al. 2000). Large values of $K_{fs}$ indicate preconcentration of analyte in the polymer matrix, with typical $logK_{fs}$ values for organic compounds such as polycyclic aromatic hydrocarbons (PAHs) in the range of 2-5 (Mayer et al. 2000; Brown et al. 2001). As long as the polymer matrix film is less than a few millimeters thick the partitioning process equilibrates within minutes.

The selectivity patterns of polymer films such as PDMS can be altered by doping the polymer. This may be accomplished by incorporating specific chemical functional groups into the polymer at various levels. For example, a PDMS film doped with phenyl groups was shown to have affinity for the aromatic compound toluene (Matejec et al. 2003).

SPME based on polymer coatings on optical fibers has been used for detection of extracted compounds through absorption of the evanescent radiation in the SPME coating (Krska et al. 1993; Mizaikoff 1999). PDMS is a good matrix for these measurements due to its optical properties: it is clear and has a refractive index (typically 1.41) which acts as a cladding to maintain light propagation in the waveguide. The main drawback of these approaches has been the need for direct absorption of radiation by the extracted compounds. This places significant limitations on the light sources and detectors which can be used.

An alternative is to measure a more generic parameter from the polymer film, such as film refractive index. This is different than the evanescent detection scheme mentioned above, as detection of refractive index changes requires detecting changes in the light propagating in the waveguide. As compounds are extracted into the film, the refractive index of the film and signal propagated through the waveguide will change, and this has been used to detect extracted compounds (Tobiska et al. 1998; Chomat et al. 2002). Problems with this approach are the poor sensitivity of the refractive index measurements used, and the lack of selectivity of the polymers used.

According to a first aspect of the invention, there is provided a method for detecting one or more compounds of interest in a test medium, using an optical sensor comprising a LPG and a SPME film. The method comprises exposing the optical sensor to the test medium such that said one or more compounds of interest are selectively partitioned into the solid phase microextraction film, and comparing at least one optical property of the sensor exposed to the test medium with at least one corresponding optical property of the sensor in absence of the test medium, wherein the comparison is indicative of detection of the one or more compounds of interest. The invention also provides an optical sensor comprising a LPG and a SPME film, and a system for carrying out the method of detecting one or more compounds of interest.

According to the invention, the SPME film is applied to the entire LPG, or a portion of the LPG. The combination of LPG and SPME coating provides for determining optical properties of the coating, which affect the optical spectrum of the LPG. In some applications it may be that a change in an optical property of the coating (e.g., refractive index) is related to the optical property of the analyte (e.g., refractive index of analyte), but this is not necessarily the case.

As used herein, the term "detecting" is intended to mean determining the presence and/or concentration and/or identity and/or optical property(ies) of one or more compounds of interest (i.e., one or more analytes).

As used herein, the term "test medium" is intended to refer to any medium in which one or more compounds of interest may be found, and which may substantially surround the optical sensor so as to facilitate detection of the analyte(s). A test medium may be solid, semi-solid, or fluid such as liquid or gas.

This aspect of the invention provides for determination of the presence, concentration, optical properties, and/or identity of an analyte partitioned into the SPME film, using the resulting shift in optical loss spectrum of the LPG. This may be determined either by recording a spectrum of wavelengths or by recording the loss at a fixed wavelength. SPME provides not only selectivity for the analyte, but also enhances the local concentration of the analyte in the film by many orders of magnitude (e.g., 100 to 1000-fold).

The chemical selectivity of the measurement arises from the chemical specificity (i.e., formulation) of the SPME film. Thus, the formulation of the film may be prepared so as to maximize selectivity for an analyte of interest. In one embodiment, the SPME film is a polymer, for example, PDMS. Such embodiment is particularly well suited to aqueous mixtures of compounds. In various embodiments, the selectivity of a SPME material may be enhanced by providing for specific chemical or physical interactions of the analyte with the polymer matrix. For example, the SPME material may be doped with, e.g., functional groups to enhance specificity to an analyte (see Example 4). In other embodiments, the film may be a polymer or composite material selected from those listed in Table 1, with corresponding selectivity to various analytes as shown. In further embodiments, the SPME film is a material or combination of materials selected from, for example, polymers, zeolites, porous glass, antibodies, ion exchange resins, solgels, and ligands.

The selectivity of a measurement may be enhanced by multiplexing two or more LPG-SPME sensors into a sensor array, and using for example, multivariate analysis to extract chemical composition of mixtures.

TABLE 1

Materials suitable for use as SPME films, and corresponding analytes (Bulletin 923, Supelco Inc., Bellefonte, PA 16823).

| SPME Coating | Application |
|---|---|
| 100 μm polydimethylsiloxane | For Volatiles |
| 7 μm polydimethylsiloxane | For Nonpolar High Molecular Weight Compounds |
| 85 μm polyacrylate | For polar semivolatiles |
| 30 μm polydimethylsiloxane | For Nonpolar Semivolatiles |
| 65 μm polydimethyl-siloxane/divinylbenzene | For Volatiles, Amines, and Nitroaromatic Compounds |

TABLE 1-continued

Materials suitable for use as SPME films, and corresponding analytes (Bulletin 923, Supelco Inc., Bellefonte, PA 16823).

| SPME Coating | Application |
| --- | --- |
| 65 μm Carbowax/divinylbenzene | For Alcohols and Polar Compounds |
| 60 μm polydimethyl-siloxane/divinylbenzene | For Amines and Polar Compounds (HPLC use only) |
| 50 μm Carbowax/templated resin | For Surfactants (HPLC use only) |
| 75 μm Carboxen/polydimethylsiloxane | For Gases and Low Molecular Weight Compounds |
| 65 μm polydimethyl-siloxane/divinylbenzene | For Volatiles, Amines, and Nitroaromatic Compounds |
| 50/30 μm divinylbenzene/Carboxen | For Flavor Compounds (Volatiles and Semivolatiles) |
| 85 μm Carboxen/polydimethylsiloxane | For Gases and Low Molecular Weight Compounds |
| 70 μm Carbowax/divinylbenzene | For Alcohols and Polar Compounds |
| 100 μm polydimethylsiloxane | For Volatiles |
| 50/30 μm divinylbenzene/Carboxen | For Odor Compounds |

According to a preferred embodiment, SPME using polymer films is optimized to achieve three objectives:

(i) A polymer matrix with a refractive index close to the refractive index of the fiber is used, so that the shift in the attenuation spectrum is maximized.

(ii) SPME increases the analyte concentration near the fiber cladding by two or three orders of magnitude over the analyte concentration in the mixture. This leads to large changes in the refractive index of the polymer matrix which are directly dependent on the concentration change in solution.

(iii) Polymers with affinities to particular classes of chemicals are used, which provides crude chemical selectivity. The effect may be enhanced by multiplexing an array of two or more of such sensors, each with slightly different polymer selectivities, and extracting the exact composition using multivariate analysis.

Fiber-loop ring-down spectroscopy (FLRDS) is capable of measuring very small changes in optical losses in optical waveguides. The technique is fully compatible with single mode optical fibers typically used for LPGs. In a single-path experiment FLRDS allows for measurement of absolute optical loss independently of power fluctuations of the light source. In one embodiment, referred to herein as "pulsed FLRDS", described in detail in our U.S. Pat. No. 6,842,548, issued Jan. 11, 2005, and in Brown et al. (2002), a nanosecond laser pulse is injected into an optical waveguide loop and the optical losses are determined from the time it takes for the intensity of the round trip signal to decay to 1/e of its initial value, i.e., the ring-down time. The technique is very robust and inexpensive. A recent improvement, described in detail in our U.S. patent application Ser. No. 11/079,478, filed on Mar. 15, 2005, and in Tong et al. (2004), involves the use of an intensity-modulated continuous wave (cw) laser beam that is coupled into the fiber. The ring-down time is obtained indirectly from the difference in the phase of the light injected and emitted from the loop. This phase shift is related to the ring-down time, $\tau$, through the relation:

$$\phi = \phi_0 + \tan^{-1}(-\Omega\tau) \quad \text{(equation 2)}$$

where $\Omega$ is the modulation frequency and $\phi_0$ is a frequency dependent offset phase angle that depends on the inherent time delays in the electronic and optical components. Depending on the intensity of the emitted light, the phase angle measurements can be done very fast and we have demonstrated a time resolution of 200 ms on a system that was not optimized.

According to a second aspect of the invention, there is provided a method for detecting one or more compounds in a test medium, comprising providing an optical sensor comprising a long period grating, measuring and comparing at least one optical property of the sensor exposed to the test medium with at least one corresponding optical property of the sensor in absence of the test medium, said comparison being indicative of detection of the one or more compounds, wherein measuring at least one optical property comprises using fiber loop ring-down spectroscopy. The invention also provides a system for carrying out such method.

This aspect of the invention provides for determination of optical loss introduced into an optical fiber loop by the LPG, using pulsed or phase shift FLRDS. As such optical loss may be caused by variables such as mechanical (e.g., stress, strain, vibration) and/or environmental (e.g., chemical, thermal) factors acting on the LPG, the invention provides a method and apparatus to accurately and rapidly detect, characterize, and/or quantify those factors. Measurements may be carried out by scanning the light source and determining the resulting spectrum in relation to such variable(s), or by keeping the light source wavelength constant and determining optical loss resulting from such variable(s) after calibration.

It should be noted that both refractive index and evanescent wave absorption change the loss properties of the LPG. For example, the refractive index change induced by the analyte may shift the attenuation band of the LPG into the wavelength region interrogated by FLRDS (or any other means of interrogating the LPG), thereby increasing the loss at this wavelength. When the laser is tuned to the wavelength where the attenuation band of the LPG is maximum in absence of the analyte, then the shift of the attenuation spectrum of the LPG in the presence of the analyte will cause the loss to decrease at this wavelength.

A benefit of this aspect of the invention is that the optical loss of the LPG can be obtained without having to rely on the linearity and stability of the light source or detector, making the system considerably more robust and field-suitable when compared to a typical intensity-based measurement. Another benefit is that FLRDS has the greatest sensitivity at low optical losses, compared to most other optical loss measurements. Further, FLRDS can be implemented using either a scanning laser source or a fixed wavelength source. In the former case, one can obtain the full attenuation spectrum with particular sensitivity to regions of low optical loss, whereas the latter case may be more suitable in a field-deployable application. Here the changes in optical loss are monitored by FLRDS in accordance with the variation of an environmental parameter, for example, the refractive index of the medium surrounding the LPG.

According to a third aspect of the invention there is provided a method for detecting one or more compounds in a test medium, comprising providing an optical sensor comprising a long period grating and a solid phase microextraction film, exposing the optical sensor to the test medium such that said one or more compounds of interest are selectively partitioned into the solid phase microextraction film, and measuring and comparing at least one optical property of the sensor exposed to the test medium with at least one corresponding optical property of the sensor in absence of the test medium, the comparison being indicative of detection of the one or more compounds, wherein measuring at least one optical property comprises using fiber loop ring-down spectroscopy. The invention also provides sensors and systems for carrying out such method.

According to this aspect of the invention, FLRDS is used to determine optical loss introduced into the optical loop by the LPG, the optical loss resulting from partitioning of an analyte into the SPME film of the LPG. FLRDS may be used as described above; that is, in phase shift or pulsed operation, scanning the light source or keeping it at a constant wavelength, and the like. The LPG and SPME are used as described above, wherein the chemical selectivity of the measurement arises from the chemical specificity of the SPME formulation, which may be enhanced as described above.

The invention is further described by way of the following non-limiting examples.

WORKING EXAMPLES

Example 1

Sensor Using a Long Period Grating and Fiber Loop Ring-Down Spectroscopy

Experimental Setup

Figure 2:
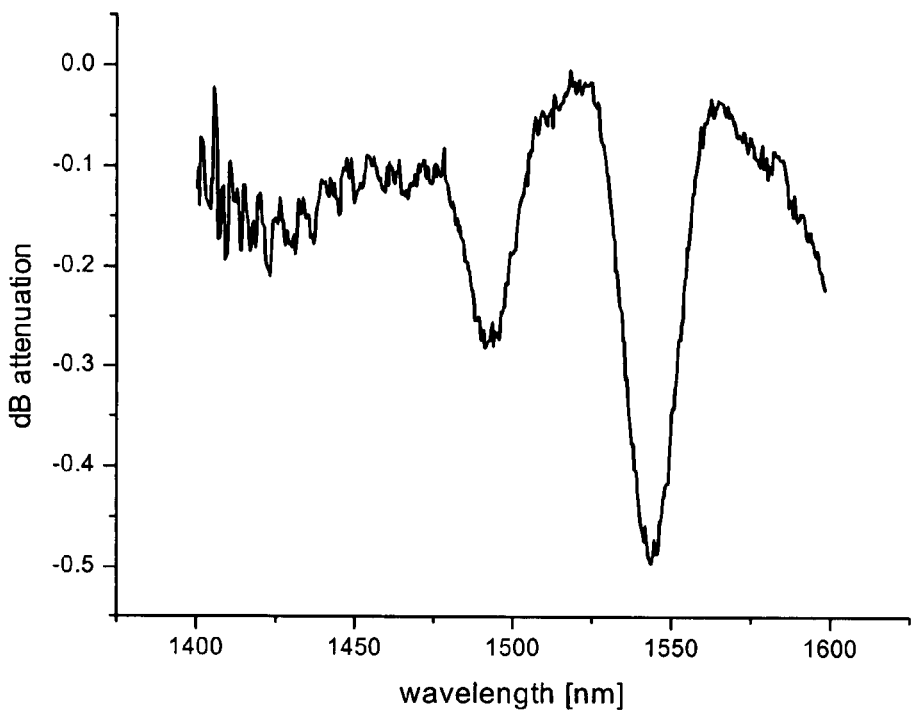
FIG. 2 is plot of the transmission spectrum in air of the LPG which was spliced into the fiber loop of the setup shown in FIG. 1.

The experimental setup is shown in FIG. 1. At its center is a LPG 10, with a length of 22 mm and a periodicity of 274 μm, which was custom-made by Avensys Inc. (Pointe-Claire, Quebec, Canada) using Dow Corning SMF-28 single mode optical fiber. The attenuation spectrum of the LPG in air at around 1.5 μm is shown in FIG. 2. The LPG was spliced into a loop 12 made of the same SMF-28 fiber using a fusion splicer to make a total length of the loop of about 11 m. An ANDO AQ4320D tunable diode laser 14 was modulated using a function generator 24, and the amplitude modulated light with a power of 5 mW and a bandwidth of 200 MHz was coupled into the loop using a 99.5/0.5 2×2 directional coupler 16 (Lightel Technologies). The intensity of light circulating within the loop was monitored using a 99.5/0.5 2×1 tap 18 (Lightel Technologies) and a fast InGaAs photodiode detector 20.

The phase angle shift, $\phi$, was measured using a 200 MHz lock-in amplifier 22 (Stanford Research Systems 844), where the reference was obtained from the synchronized output of the modulated laser diode. The error in the measurements was approximately 0.02 degree according to the manufacturer. The ring-down time of the fiber loop was determined from the slope of a plot of tan $\phi$ against the modulation frequency, $\Omega$ (Tong et al. 2004).

The inset in FIG. 1 shows shematically analyte particles partitioning into an SPME film disposed on the LPG, as described in Example 3.

Results

Figure 3:
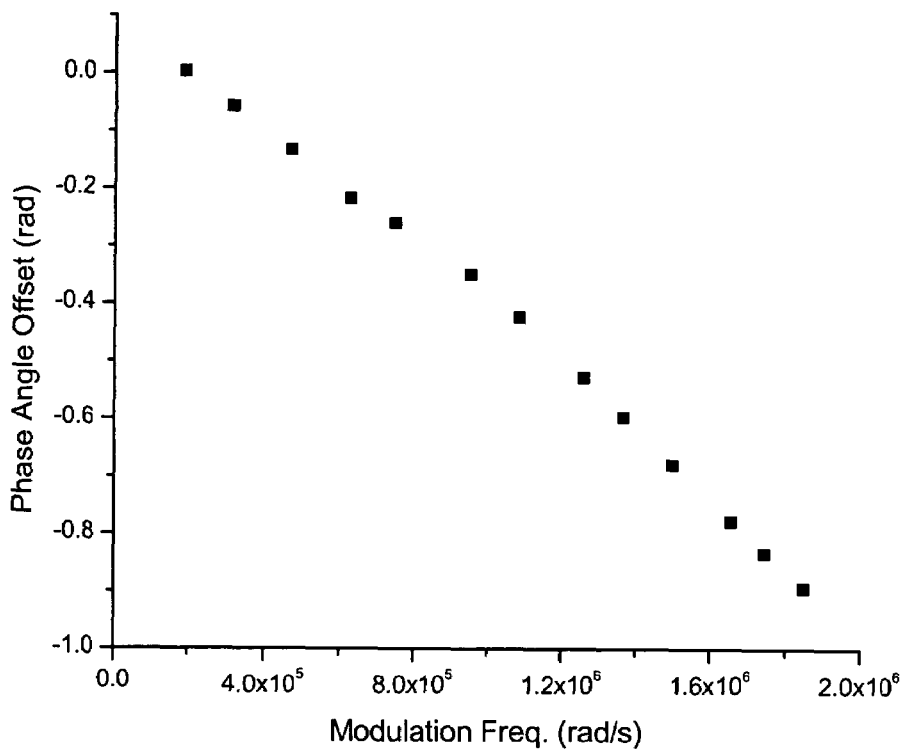
FIG. 3 is a plot of the instrumental phase angle offset correction. The fiber loop connecting the laser and detector (see FIG. 1) was replaced by a patch consisting of a short length of SMF-28 optical fiber. The modulation frequency dependent phase shift between the photodiode detector signal and the laser modulation constitutes an instrumental correction factor which must be subtracted from phase shift measurements made using the fiber loop.

To obtain reliable optical decay constants from the FLRDS measurement, one needs to determine the time-response and offset phase angle of the instrumentation. Using a patch cord to couple the laser output straight into the light detector, the frequency-dependent instrumental phase offset was measured (FIG. 3).

Figure 4:
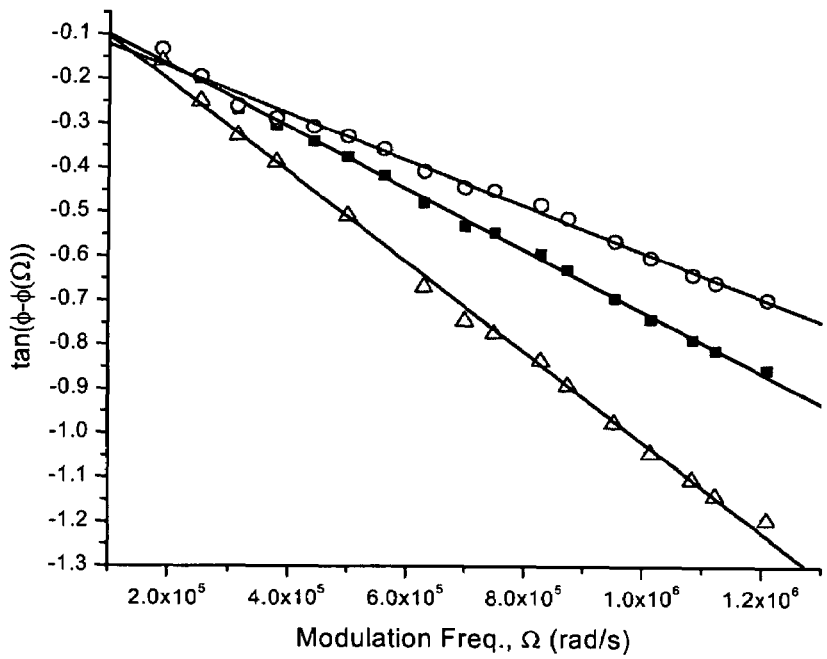
FIG. 4 is a plot of modulation frequency dependence of the phase angle difference between the fiber loop of FIG. 1 and the patch used to obtain the data in FIG. 3, at three different laser frequencies. The slope of these plots gives the negative ring-down time for the fiber loop. Triangles, 1520 nm without the LPG in the loop; squares, 1520 nm with the LPG in the loop; circles, 1527 nm with the LPG in the loop.

In the absence of any offsets, the tangent of the phase angle should vary linearly with the modulation frequency and the slope will yield the ring-down time, $\tau$. It was found that both frequency dependent and frequency independent offsets needed to be included. The ring-down times were obtained using this correction. The ring-down time measured at 1520 nm without the LPG (FIG. 4; triangles) was 998 ns. With the LPG in the loop (squares), the ring-down time at 1520 nm was 683 ns, while that measured at 1527 nm (circles) was 520 ns. Examination of FIG. 2 indicates that the higher loss of the LPG at 1527 nm compared with that at 1520 nm is responsible for the shorter ring-down time at this laser wavelength.

Figure 5A:
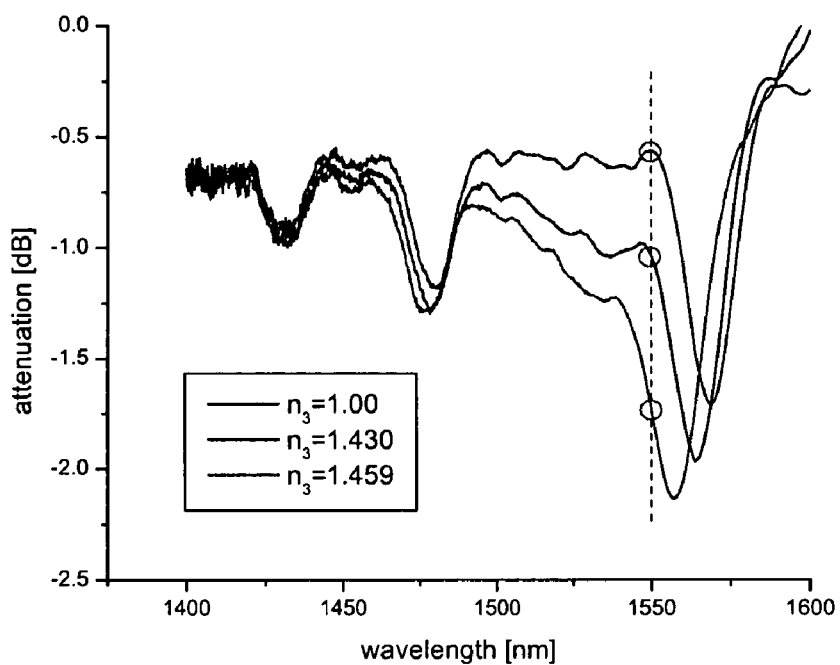
FIG. 5A is a plot showing the attenuation spectra of a LPG with periodicity of $\Lambda=274$ μm submersed in three DMSO solutions with different refractive index.
Figure 5B:
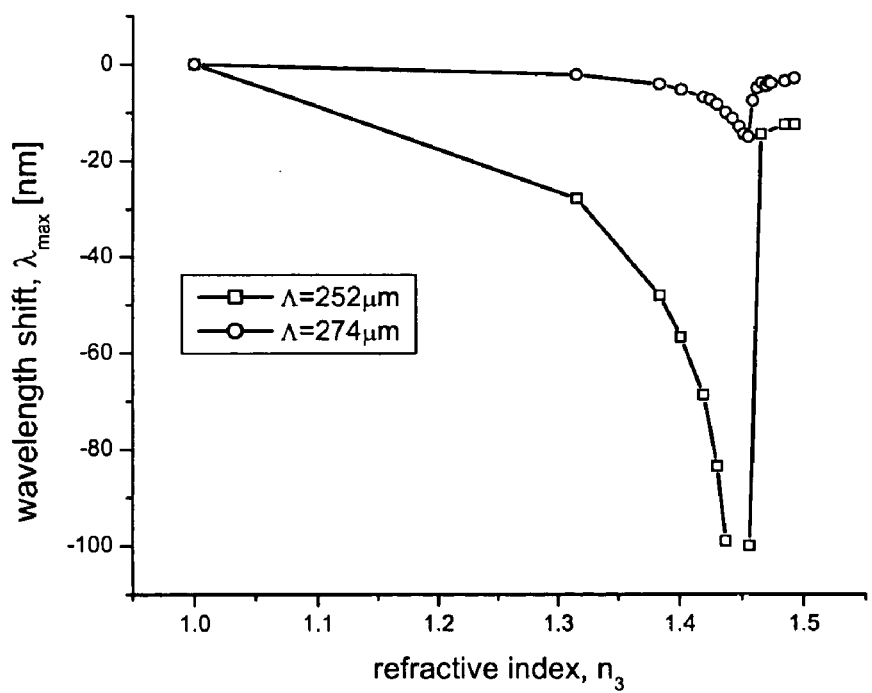
FIG. 5B is a plot showing change in attenuation maximum wavelength with refractive index for two LPGs with different periodicities, as indicated. The attenuation maximum at around 1570 nm of the LPG used in FIG. 5A shifts by about 16 nm as the refractive index of the surrounding solution is changed to match the refractive index of the cladding. The periodicity affects the sensitivity of the monitored mode to refractive index, seen as a greater wavelength response for the 252 µm LPG. The maximum wavelength response is when the refractive index approaches the refractive index of the cladding independent of the periodicity.

The effect of a change of refractive index in the attenuation spectrum of the LPG was determined by immersing the LPG in solutions of dimethylsulfoxide (DMSO) in water where the mole fraction was modified from 30% to 100% in DMSO. From the mole fraction the refractive index was calculated using the Lorentz-Lorenz equation. FIG. 5A shows the effect of the surrounding refractive index on the attenuation spectrum. The attenuation maxima corresponding to higher order cladding modes (maxima at longer wavelengths) shift dramatically as the refractive index of the surrounding solution approaches and then matches the refractive index of the cladding.

Figure 6:
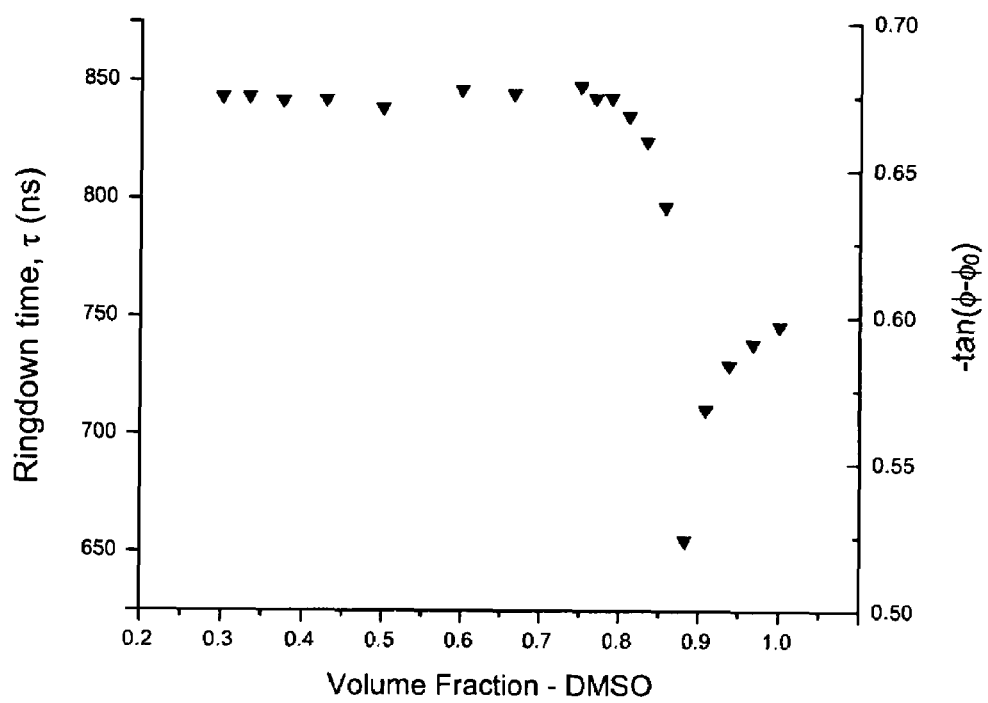
FIG. 6 is a plot showing dependence of the fiber loop ring-down time on the composition of a solution surrounding the LPG, obtained using the setup of FIG. 1. The volume fraction of a solution containing dimethylsulfoxide (DMSO) and water surrounding the LPG was varied and the cavity ring-down time was determined. The solution temperature was 22° C. The laser wavelength was set at 1520 nm and the modulation frequency was 130 kHz.

As can be seen from FIGS. 5A and B, the optical losses change dramatically as the refractive index changes. For example, FIG. 5A shows that the optical losses at 1550 nm increase by more than 1 dB as the refractive index of the surrounding solution increases. We therefore kept the laser wavelength fixed at 1520 nm, spliced the LPG into the fiber loop and measured the optical loss through the phase angle for different mole fractions of DMSO and water (FIG. 6). In the region of maximum slope, a change in refractive index of 0.000015 can be detected assuming a phase resolution of 0.02°.

Without being bound to any particular theory at the exclusion of others, one explanation for the shape of the curve in FIG. 6 is that, as the volume fraction of DMSO increases, the ring-down time decreases sharply as the refractive index of the test medium approaches that of the optical fiber cladding. As the volume fraction of DMSO increases further, the ring-down time increases as the refractive index of the test medium exceeds that of the optical fiber cladding.

Example 2

Sensor Using a Long Period Grating and Solid Phase Microextraction

Figure 7A:
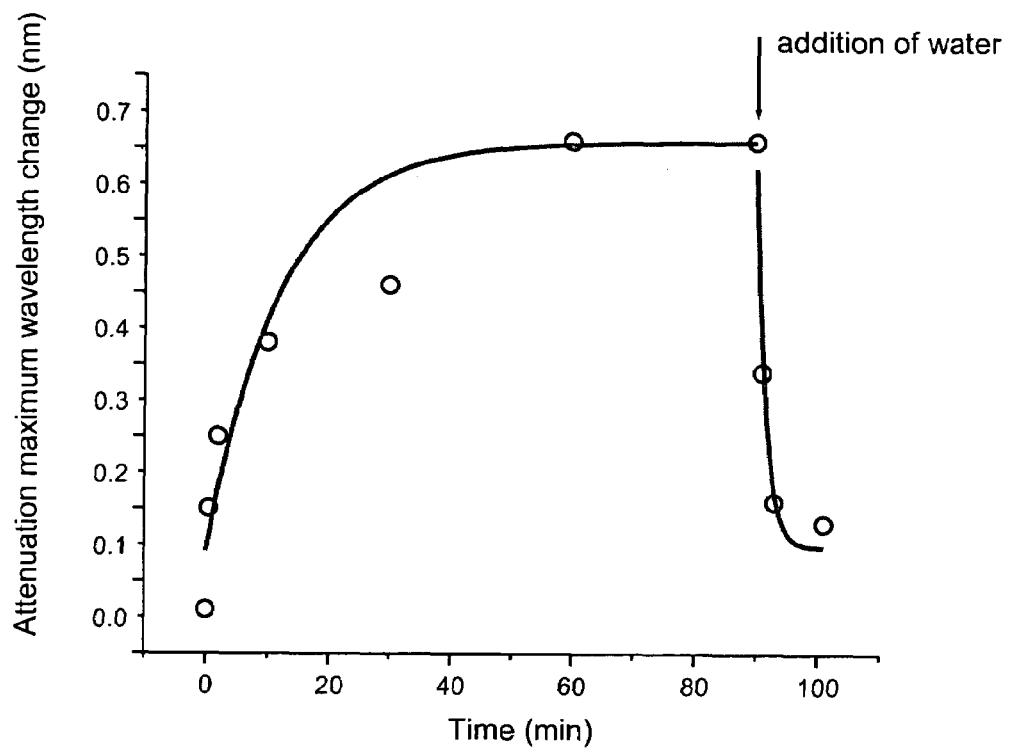
FIG. 7A is a plot showing temporal evolution of the position of the attenuation maximum of a LPG. The entire LPG was coated with a thin film of PDMS and submersed in a saturated solution of toluene in water. As the toluene partitioned into the PDMS the refractive index of the PDMS matrix increased and consequently the attenuation spectrum shifted. The solid curves are exponential rise and decay curves with time constants of 19 min and 1.55 min, respectively.

The combination of solid-phase microextraction with long period gratings but without the use of optical ring-down detection was tested in a preliminary experiment. An LPG was coated with PDMS (Dow Corning 100% silicone rubber) by evaporating the solvent from a 100 mg/ml solution of the PDMS precursor material in methylene chloride. The thickness of the resulting film was estimated to be between 10 and 500 μm and its refractive index was close to $n_3=1.41$ (Chomat et al. 2002). Attenuation spectra of the LPG were recorded in straight transmission while the film was submersed in a saturated solution of toluene in water (concentration approx. 500 ppm). The change in position of the attenuation maximum was recorded as a function of time (FIG. 7A) and was fitted using a simple exponential growth function. A partitioning time constant of $t_{fs}=19$ min was obtained for partitioning of toluene into the polymer and of only 1.55 min for removal of toluene during rinsing with water. The concentration of the toluene in the PDMS can be estimated using the octanol-water partitioning coefficient ($pK_{ow}=2.7$). Given that the concentration in water was about 500 ppm, its concentration in PDMS was estimated to be close to 1%. The long apparent equilibration time in saturated toluene is attributed to slow swelling of the polymer film.

Figure 7B:
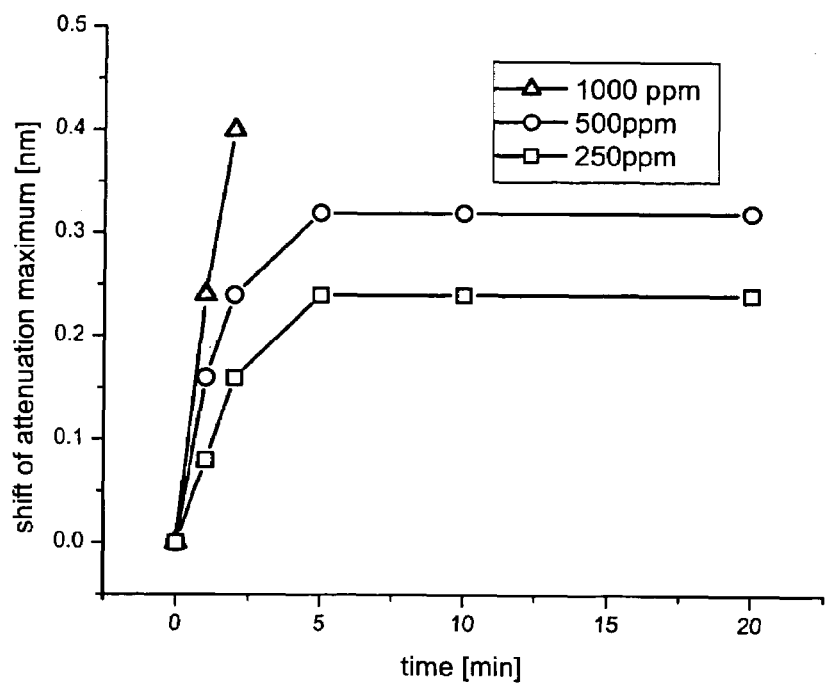
FIG. 7B shows temporal evolution of the attenuation maximum wavelength for lower concentrations of toluene for the LPG of FIG. 7A, with equilibration in about 5 min. The shift in wavelength after 5 min exposure is linearly related to the toluene concentration (data not shown). The signal did not stabilize at 1000 ppm toluene concentration.
Figure 7C:
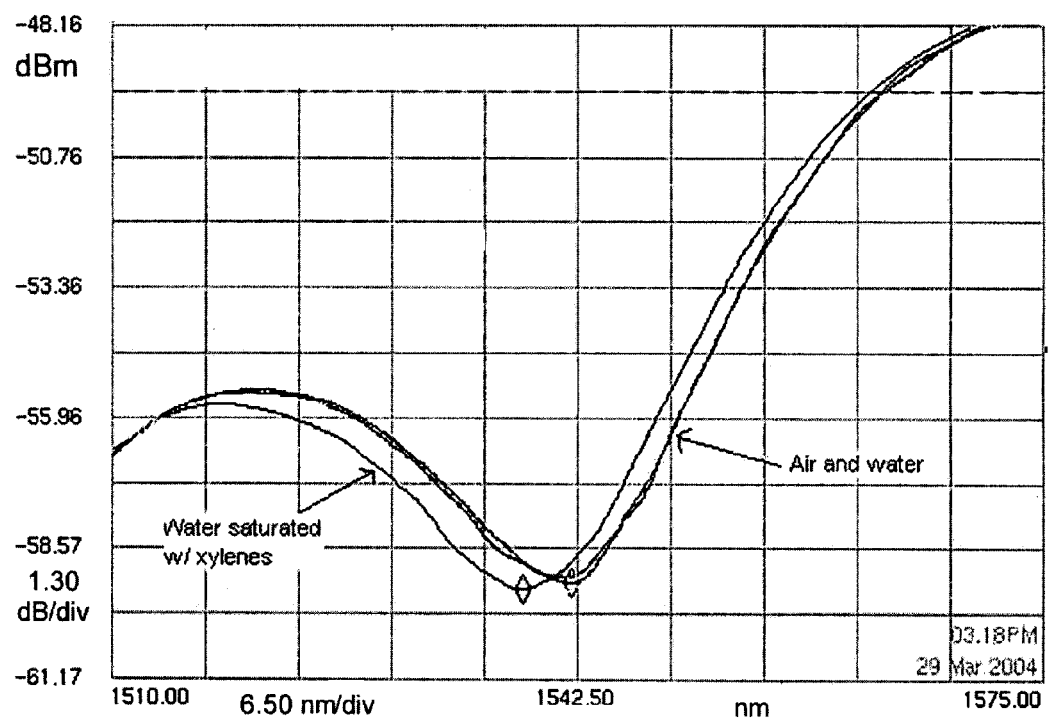
FIG. 7C is a plot of spectra of an LPG coated with a film of PDMS, measured upon immersion in air, water and after submersion in a saturated solution of xylenes (mixture of isomers) in water.

Exposure to lower toluene concentrations provided more rapid equilibration (5 min) with smaller wavelength shifts (FIG. 7B). The shift after 5 min was linearly proportional to the concentration of the toluene in the water. A similar wavelength shift was observed on addition of xylenes (mixture of isomers) in water, as seen in FIG. 7C.

Example 3

Sensor Using a Long Period Grating, Solid Phase Microextraction, and Fiber Loop Ring-Down Spectroscopy In this example a sensor based on the combination of an LPG with SPME and interrogated by FLRDS is described. In particular, this example relates to a sensor for detecting hydrophobic contaminants in water. The inset in FIG. 1 shows shematically analyte particles partitioning into an SPME film disposed on the LPG.

Figure 8A:
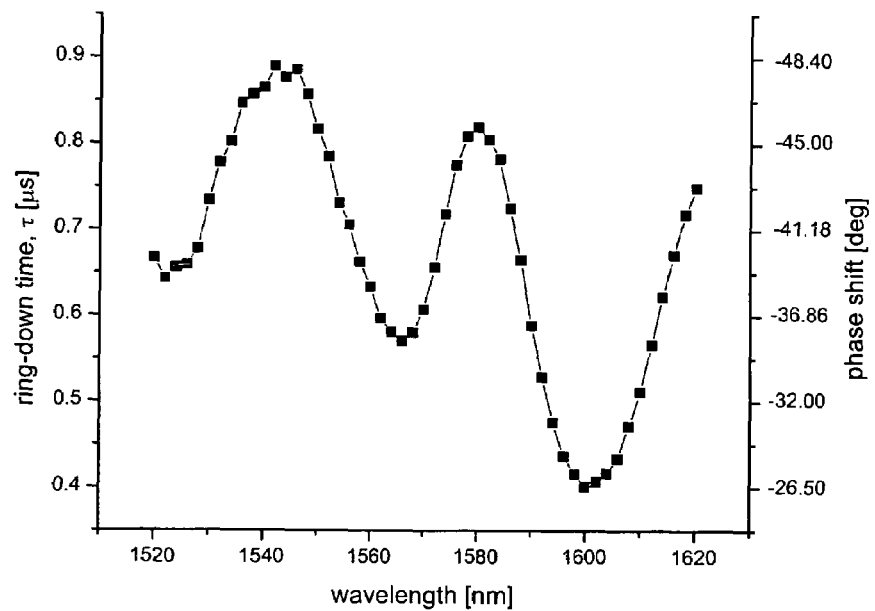
FIG. 8A is a plot of the attenuation spectrum of a LPG (Λ=282 µm) coated with a PDMS film obtained using the phase-shift optical loop ring-down technique (see description). Shown is the ring-down time in us, the phase angle difference between light entering and exiting the fiber loop as a function of laser wavelength, as well as the ring-down time in microseconds, which was determined using equation 2.

An LPG with a comparably weak attenuation spectrum was coated with PDMS (Dow Corning 100% silicone rubber) by evaporating the solvent from a 100 mg/ml solution of PDMS precursor material in methylene chloride. The thickness of the resulting film was between about 10 and 500 μm and its refractive index was close to 1.41. The attenuation spectrum of the LPG was recorded using fiber-loop ring-down spectroscopy in the continuous wave (i.e., phase shift) implementation. In particular, the phase angle of the synchronized output from a periodically driven laser was referenced to the detector output, and from the difference of the phase angles the ring-down time was calculated (FIG. 8A).

As the ring-down times were recorded over part of the attenuation spectrum of the LPG they provided for a very sensitive determination of optical loss. The attenuation spectrum was then modified by immersing the polymer-coated LPG in a test medium. For example, solutions of different concentrations of xylene in water used to evaluate the technique. Changes in the attenuation spectrum were recorded by measuring ring-down times (via phase angle differences) at many different wavelengths. From the shift of the attenuation maximum the concentration of xylene was then obtained, after calibration.

Figure 8B:
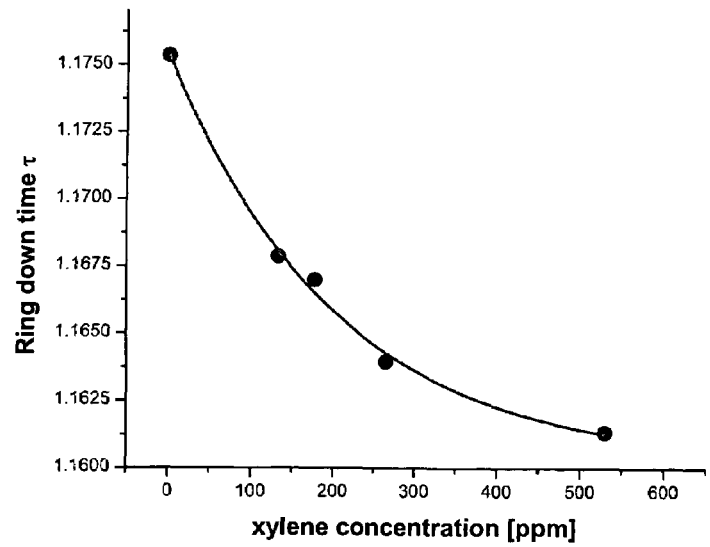
FIG. 8B is a plot of the change in ring-down time of the PDMS-coated LPG of FIG. 8A, as a function of the concentration of xylene in water. The laser wavelength was fixed at 1590 nm. As the xylene partitioned into the PDMS polymer the refractive index of the polymer changed and the spectrum shown in FIG. 8A shifted, thereby increasing the optical loss at 1590 nm.

Furthermore, the attenuation of the LPG was recorded using FLRDS at a fixed wavelength and from the ring-down time a concentration of xylene in water was obtained after calibration. In FIG. 8B the dependence of the ring down time, which was derived from the phase angle, on the xylene concentration is shown.

Example 4

Film:Solution Partition Constant ($K_{fs}$) of Modified PDMS Films

Figure 9:
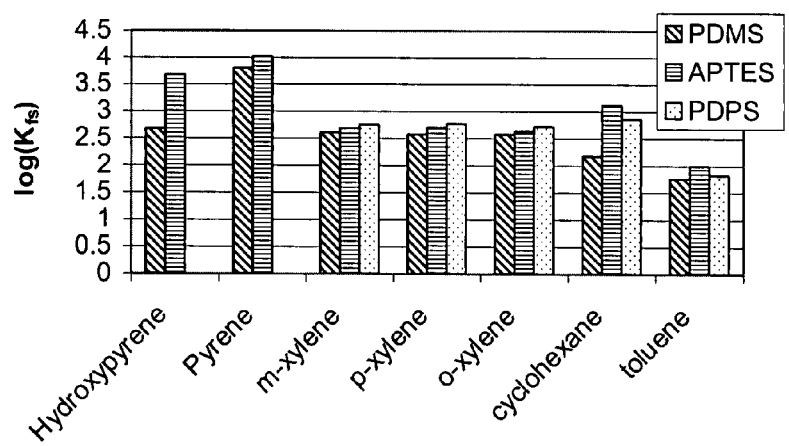
FIG. 9 shows film:solution partition constant ($K_{fs}$) values for various compounds partitioning from water into three siloxane films: pure polydimethylsiloxane (PDMS), PDMS doped with amine groups by adding 10% (v/v) 3-aminopropyltriethoxy silane to PDMS precursor before film formation (APTES), and PDMS doped with phenyl groups by adding 10% (v/v) diphenyldiethoxy silane to PDMS precursor before film formation (PDPS).

FIG. 9 shows the $logK_{fs}$ values measured for a variety of analytes in pure PDMS film and in modified PDMS films. The modified PDMS films were doped with amine groups (by adding 10% (v/v) 3-aminopropyltriethoxy silane to PDMS precursor before film formation) (APTES), and with phenyl groups (by adding 10% (v/v) diphenyldiethoxy silane to PDMS precursor before film formation) (PDPS). These results show different affinity of the three polymers for the analytes. For example, the positive effect of the amine group in the APTES polymer on hydroxypyrene partitioning is dramatic. The polar hydroxylated molecule normally partitions weakly into PDMS, but addition of the amine group provides an opportunity for specific hydrogen-bonding interactions, which dramatically increases the $K_{fs}$ value.

Example 5

Refractive Index Changes in Films

Figure 10A:
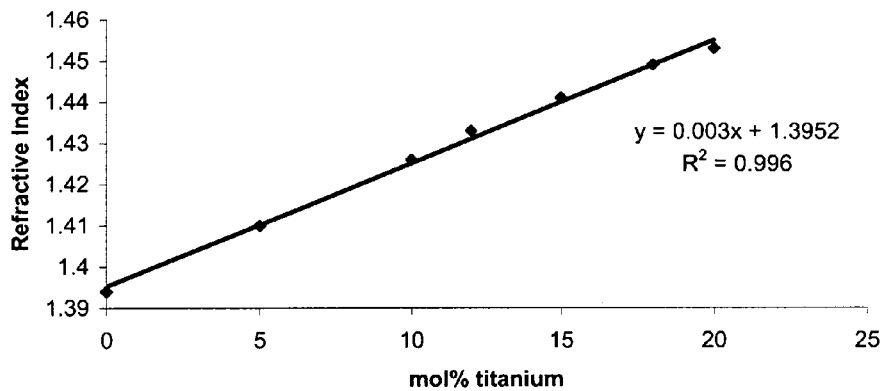
FIG. 10A is a plot showing refractive index of PDMS films as a function of the mol% of titanium doping of the PDMS. The doped PDMS was prepared by adding tetraethoxy titanium to PDMS during polymerization. Films were deposited on glass slides and refractive index was measured using a refractometer.
Figure 10B:
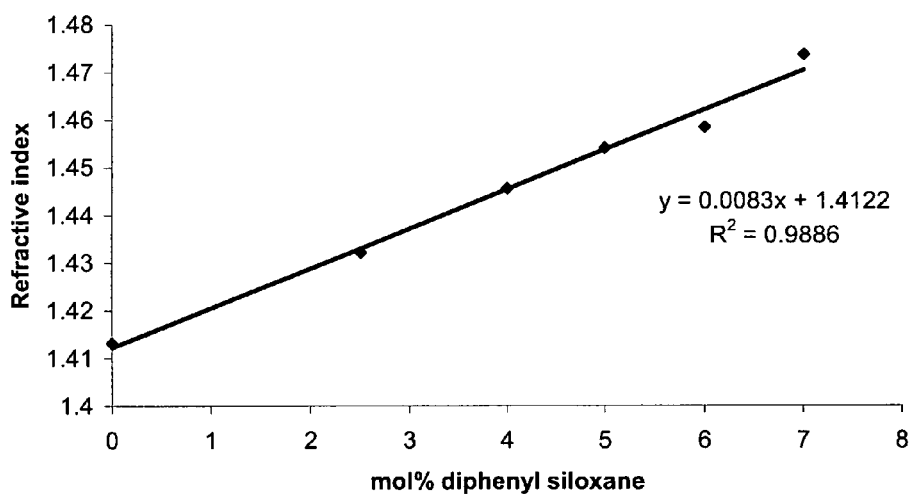
FIG. 10B is a plot showing refractive index of 6 mol% titanium-doped PDMS films as a function of mol% diphenyl siloxane doping of the PDMS. The doped PDMS was prepared by adding diethoxydiphenyl silane and tetraethoxy titanium during polymerization. Films were deposited on glass slides and refractive index was measured using a refractometer.

Table 2 shows the refractive index (at 1.55 μm wavelength) of several PDMS and modified PDMS polymer films. Modified films were made from the polymerization of dichlorodimethyl silane with one or more of the following: trichloromethyl silane, diethoxydiphenyl silane, 3-aminopropyltriethoxy silane or tetraethoxy titanium (IV). All percentages in Table 2 are in mole percent. FIG. 10 shows the ability to modify the film refractive index to a specific value by changing the levels of titanium (FIG. 10A) or diphenyl siloxane (FIG. 10B) substituent in the film.

Figure 11:
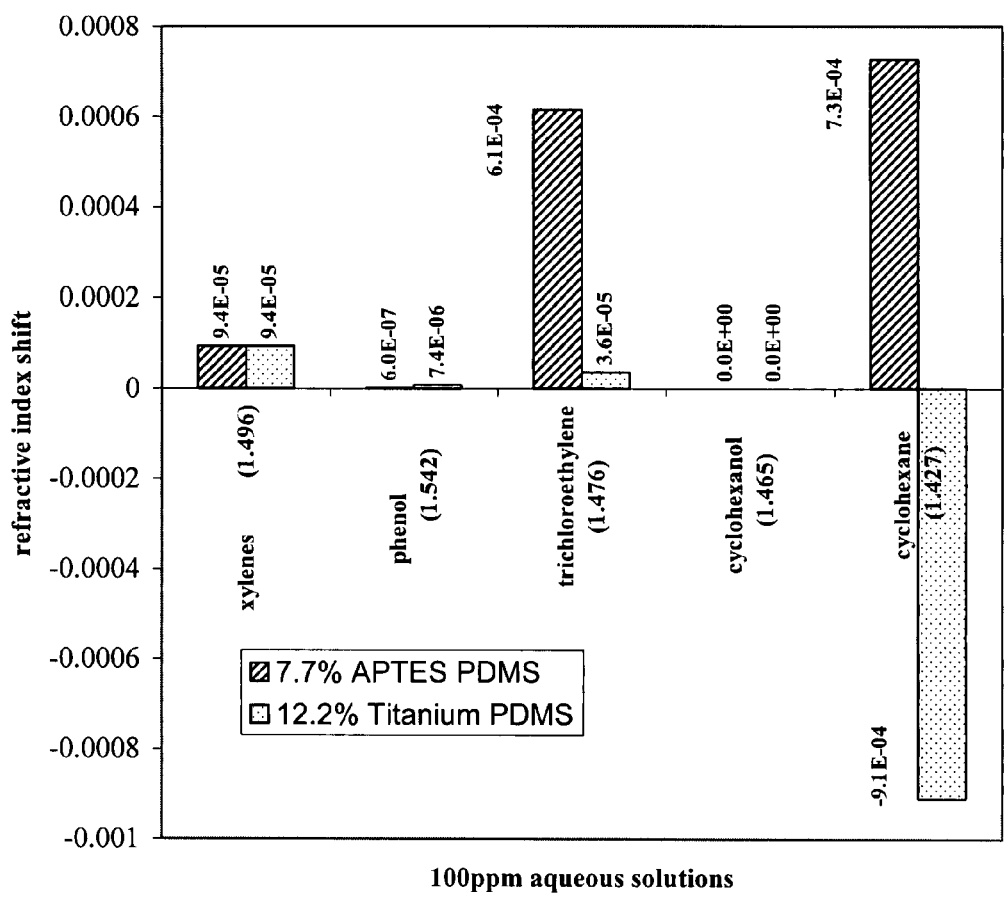
FIG. 11 shows the change in refractive index of a 12.2% titanium PDMS film, or a 7.7% APTES PDMS film, for various analytes. Films were deposited on glass slides and refractive index was measured using a refractometer. The slides were exposed to water saturated with the analyte and the change in refractive index was normalized to a 100 ppm solution concentration. The numbers in parentheses indicate the refractive index of the analytes in pure liquid form.

Partitioning of analytes into the film caused a change in the film refractive index. FIG. 11 shows changes in refractive index for various analytes partitioned into either a 12.2% titanium PDMS film, or a 7.7% APTES PDMS film. Films were exposed to water saturated with the analyte. The corresponding change in refractive index was normalized to change for a 100 ppm solution of the analyte. These results show the different responses of these two modified polymer films, which provides differentiation between analytes. Thus, an array of sensors, each with a different SPME film, which films may comprise modified and unmodified polymers such as PDMS, would provide for differential detection/identification of various analytes.

TABLE 2

Refractive index (at 1.55 μm wavelength) of several PDMS and modified PDMS polymer films. Film details are given in the text.

| Film | Refractive Index |
|---|---|
| PDMS (Dow Corning Aquarium Sealant) | 1.3961 |
| PDMS (Dow Corning Sylgard 184) | 1.4036 |
| PDMS | 1.3935 |
| PDMS (12.2% Titanium) | 1.4415 |
| PDMS (20.0% Titanium) | 1.453 |
| PDMS (7.7% APTES) | 1.4148 |
| PDMS (4.7% Diphenyl, 14.0% APTES) | 1.4373 |
| PDMS (4% Diphenyl, 6% Titanium) | 1.4456 |

Those skilled in the art will recognize, or will be able to ascertain using routine experimentation, variants of the embodiments described herein. Such variants are within the scope of the invention and are covered by the appended claims.

REFERENCES

Allsop T., Zhang L., Bennion I. (2001) Detection of organic aromatic compounds in paraffin by a long-period fiber grating optical sensor with optimized sensitivity, *Optics Communications* 191:181-190.

Bhatia V., Vengsarkar A. M. (1996) Optical fiber long-period grating sensors, *Optics Letters* 21:692-694.

Bhatia V. (1999) Applications of long-period gratings to single and multi-parameter sensing, *Optics Express* 4:457-466.

Brown R. S., Akhtar P., Akerman J., Hampel L., Kozin I.S., Villerius L. A., Klamer H. J. C. (2001) Partition controlled delivery of hydrophobic substances in toxicity tests using polydimethylsiloxane (PDMS) films, *Environmental Science and Technology*, 35:4097-4102.

Brown R. S., Kozin I., Tong Z., Oleschuk R. D., Loock H.-P. (2002) Fiber loop ring down spectroscopy, *J. Chem. Phys.*, 11,23:10444.

Chomat M., Berkova D., Matejec V., Kasik I., Kuncova G., Hayer M. (2002) Optical detection of toluene in water using an IGI optical fiber with a short sensing region, *Sensors and Actuators B* 87:258-267.

Chong J. H., Shum P., Haryono H., Yohana A., Rao M.K., Lu C., Zhu Y.N. (2004) Measurements of refractive index sensitivity using long-period grating refractometer, *Optics Communications* 229:65-69.

DeLisa M. P., Zhang Z., Shiloach M., Pilevar S., Davis C.C., Sirkis J.S., Bentley W.S. (2000) Evanescent wave long period fiber Bragg grating as an immobilized antibody biosensor, *Analytical Chemistry* 72:2895-2900.

Grubsky V., Feinberg J. (2000), Long-period fiber gratings with variable coupling for real-time sensing applications, *Optics Letters* 25:203-205.

James S.W., Tatam R. P. (2003) Optical fibre long-period grating sensors: Characteristics and application, *Measurement Science & Technology* 14:R49-R61.

Khaliq S., James S.W., Tatam R. P. (2001) Fiber-optic liquid-level sensor using a long-period grating, *Optics Letters* 26:1224-1226.

Khaliq S., James S.W., Tatam R. P. (2002) Enhanced sensitivity fibre optic long period grating temperature sensor, *Measurement Science & Technology* 13:792-795.

Krska R., Kellner R., Schiessl U., Tacke M., Katzir A. (1993) Fiber optic sensor for chlorinated hydrocarbons in water based on infrared fibers and tunable diode lasers, *Appl. Phys. Lett.* 63:4.

Lee S.T., Kumar R. D., Kumar P. S., Radhakrishnan P., Vallabhan C.P.G., Nampoori V. P. N. (2003) Long period gratings in multimode optical fibers: application in chemical sensing, *Optics Communications* 224:237-241.

Luo S., Liu Y., Sucheta A., Evans M., Van Tassell R. (2002) Applications of LPG fiber optical sensors for relative humidity and chemical warfare agents monitoring, Advanced Sensor Systems and Applications, Rao Y. J. et al., eds., *Proceedings of SPIE* 4920:193-204.

Matejec V., Chomat M., Berkova D., Mrazek J., Ardeleanu R., Harabagiu V., Pinteala M., Simionescu B. C. (2003) Detection of toluene dissolved in water by using PCS fibers excited by an inclined collimated beam, *Sensors and Actuators B* 90:204-210.

Mayer P., Vaes W. H. J., Hermens J. L. M. (2000) Absorption of hydrophobic compounds into the poly(dimethylsiloxane) coating of solid-phase microextraction fibers: high partition coefficients and fluorescence microscopy images, *Anal. Chem.* 72:459-464.

Mizaikoff B. (1999) Mid-infrared evanescent wave sensors—a novel approach for subsea monitoring, *Meas. Sci. Technol.* 10:1185-1194.

Shu X. W., Huang D. X. (1999) Highly sensitive chemical sensor based on the measurement of the separation of dual resonant peaks in a 100-mu m-period fiber grating, *Optics Communications* 171:65-69.

Tobiska P., Chomat M., Matejec V., Berkova D., Huttel I. (1998) Investigation of fiber-optic evanescent-wave sensors for detection of liquid hydrocarbons, *Sensors and Actuators B* 51:152-158.

Tong Z., Wright A., McCormick T., Loock H.-P. (2004) Phase-shift fiber-loop ring-down spectroscopy, *Anal. Chem.* 7:6594-6599.

The invention claimed is:

1. A method for detecting one or more compounds in a test medium, comprising:
    providing an optical sensor comprising a long period grating;
    providing an optical waveguide loop optically connected to said optical sensor;
    using fiber loop ring-down spectroscopy to measure and compare at least one optical property of the sensor exposed to the test medium with at least one corresponding optical property of the sensor in absence of the test medium, a result of said comparison being indicative of detection of the one or more compounds;
    wherein said fiber loop-down spectroscopy comprises:
    launching in the optical waveguide loop an intensity-modulated light at a reference phase;
    detecting a phase of said light along the optical waveguide loop; and
    comparing the detected phase of said light along the loop with the reference phase;
    wherein comparing the detected phase and the reference phase provides information about said at least one optical property of the optical sensor.

2. The method of claim 1, further comprising:
    disposing a solid phase microextraction film on the long-period grating;
    wherein said one or more compounds are selectively partitioned into the solid phase microextraction film.

3. A method for detecting one or more compounds in a test medium, comprising:
    providing an optical sensor comprising a long period grating;
    providing an optical waveguide loop optically connected to said optical sensor;
    using fiber loop ring-down spectroscopy to measure and compare at least one optical property of the sensor exposed to the test medium with at least one corresponding optical property of the sensor in absence of the test medium, a result of said comparison being indicative of detection of the one or more compounds;
    wherein said fiber loop-down spectroscopy comprises:
    illuminating the optical waveguide loop with a plurality of light pulses;
    detecting roundtrips of said light pulses at one or more locations along the loop; and
    determining ring-down time of said light pulses;
    wherein said ring-down time is indicative of at least one optical property of the optical sensor.

4. The method of claim 3, further comprising:
    disposing a solid phase microextraction film on the long-period grating;
    wherein said one or more compounds are selectively partitioned into the solid phase microextraction film.

5. A system for detecting one or more compounds in a test medium, comprising:
    an optical sensor comprising a long period grating, the optical sensor having at least one optical property which is altered when exposed to the one or more compounds;
    an optical waveguide loop optically connected to said optical sensor;
    a light source for launching a light in the optical waveguide loop;
    a photodetector for detecting said light along the optical waveguide loop, said light having passed though the optical sensor; and
    means for analyzing the detected light;

wherein the detected light provided information about said at least one optical property of the optical sensor.

6. The system of 5, wherein:

the light source launches an intensity-modulated light at a reference phase;

the photodetector detects a phase of said light along the optical waveguide loop; and means for analyzing comprises means for comparing the detected phase of said light along the loop with the reference phase;

wherein comparing the detected phase and the reference phase provides information about said at least one optical property of the optical sensor.

7. The system of claim 5, wherein:

the light source illuminates the optical waveguide loop with a plurality of light pulses;

the photodetector detects roundtips of said light pulses at one or more locations along the loop; and means for analyzing comprises means for determining ring-down time of said light pulses;

wherein ring-down time is indicative of at least one optical property of the sensor.

8. The system of claim 5, further comprising a solid phase microextraction film disposed on said long period grating;

wherein the one or more compounds are selectively partitioned into the solid phase microextraction film; and wherein the partitioning of the one or more compounds alters at least one optical property of the long period grating.

9. The system of claim 8, wherein partitioning of the one or more compounds of interest into the solid phase microextraction film is reversible.

10. The system of claim 5, wherein the at least one optical property is refractive index.

11. The system of claim 5, wherein the light has at least one wavelength selected from infra-red (IF), visible, and ultraviolet.

12. The system of claim 5, wherein the optical waveguide loop comprises a single-mode optical fiber.

13. The system of claim 5, wherein the optical sensor comprises an array of two or more long period gratings each including a solid phase microextraction film.

* * * * *

UNITED STATES PATENT AND TRADEMARK OFFICE
CERTIFICATE OF CORRECTION

PATENT NO.         : 7,391,942 B2                                    Page 1 of 1
APPLICATION NO.    : 11/145182
DATED              : June 24, 2008
INVENTOR(S)        : Hans-Peter Loock et al.

It is certified that error appears in the above-identified patent and that said Letters Patent is hereby corrected as shown below:

Column 16, Line 50
"film on the long-" should be --film on the long--

Column 16, Line 65
"passed though" should be --passed through--

Column 17, Line 1
"light provided" should be --light provides--

Column 17, Line 3
"of 5," should be --of claim 5,--

Column 17, Line 17
"detects roundtips" should be --detects roundtrips--

Column 17, Line 22
"property of the sensor." should be --property of the optical sensor.--

Column 18, Line 5
"wherein the partitioning" should be --wherein partitioning--

Signed and Sealed this

Sixth Day of October, 2009

David J. Kappos
*Director of the United States Patent and Trademark Office*